United States Patent [19]

Okamoto et al.

[11] 4,072,757

[45] * Feb. 7, 1978

[54] N²ALKOXYNAPHTHYLSULFONYL-L-ARGININAMIDES AND THE PHARMACEUTICALLY ACCEPTABLE SALTS THEREOF

[75] Inventors: Shosuke Okamoto, 15-1i, Asahigaoka 3-chome, Tarumi, Kobe, Hyogo, Japan; Akiko Hijikata, Kobe, Japan; Ryoji Kikumoto, Machida, Japan; Yoshikuni Tamao, Yokohama, Japan; Kazuo Ohkubo, Machida, Japan; Tohru Tezuka, Yokohama, Japan; Shinji Tonomura, Tokyo, Japan

[73] Assignees: Mitsubishi Chemical Industries Limited, Tokyo; Shosuke Okamoto, both of Japan

[*] Notice: The portion of the term of this patent subsequent to Feb. 1, 1994, has been disclaimed.

[21] Appl. No.: 760,587

[22] Filed: Jan. 19, 1977

Related U.S. Application Data

[63] Continuation-in-part of Ser. No. 653,217, Jan. 28, 1976, which is a continuation-in-part of Ser. No. 671,436, March 29, 1976, which is a continuation-in-part of Ser. No. 622,390, Oct. 14, 1975, abandoned.

[30] Foreign Application Priority Data

| Nov. 8, 1974 | Japan | 49-128774 |
|---|---|---|
| Nov. 8, 1974 | Japan | 49-128775 |
| Nov. 29, 1974 | Japan | 49-136695 |
| Nov. 29, 1974 | Japan | 49-136697 |
| Feb. 25, 1975 | Japan | 50-023268 |
| Feb. 26, 1975 | Japan | 50-023635 |
| Mar. 5, 1975 | Japan | 50-026768 |
| Mar. 11, 1975 | Japan | 50-029357 |
| Mar. 11, 1975 | Japan | 50-029358 |

[51] Int. Cl.² .................. A61K 31/445; C07D 211/60
[52] U.S. Cl. ............................ 424/267; 260/112.5 R; 260/293.62; 424/177
[58] Field of Search ................... 260/112.5 R, 293.62; 424/177, 267

[56] References Cited

U.S. PATENT DOCUMENTS

| 3,622,615 | 11/1971 | Nicolaides et al. | 260/470 |
| 3,978,045 | 8/1976 | Okamoto et al. | 260/239 B |

*Primary Examiner*—Richard L. Raymond
*Attorney, Agent, or Firm*—Oblon, Fisher, Spivak, McClelland & Maier

[57] ABSTRACT

N²-alkoxynaphthylsulfonyl-L-argininamides and the pharmaceutically acceptable salts thereof have been found to be effective as pharmaceutical agents for the inhibition and suppression of thrombosis in mammals.

4 Claims, No Drawings

N²-ALKOXYNAPHTHYLSULFONYL-L-ARGININA-MIDES AND THE PHARMACEUTICALLY ACCEPTABLE SALTS THEREOF

CROSS-REFERENCE TO RELATED APPLICATIONS

This application is a continuation-in-part of U.S. application Ser. No. 653,217 filed Jan. 28, 1976, which, in turn, is a continuation-in-part of U.S. Ser. No. 671,436 filed Mar. 29, 1976 which, in turn, is a continuation-in-part of U.S. Ser. No. 622,390 filed Oct. 14, 1975, now abandoned.

BACKGROUND OF THE INVENTION

1. Field of the Invention

This invention relates to the discovery of certain new and useful N²-alkoxynaphthylsulfonyl-L-argininamides and the pharmaceutically acceptable salts thereof, which are of especial value in view of their outstanding antithrombotic properties and low toxicities.

2. Description of the Prior Art

In the past, there have been many attempts to obtain new and improved agents for the treatment of thrombosis. The N²-(p-tolylsulfonyl)-L-arginine esters have been found to be one type of agent which can be used and these have been found to be effective in dissolving blood clots. (U.S. Pat. No. 3,622,615, issued Nov. 23, 1971) One family of compounds, which have been found to be particularly useful as highly specific inhibitors of thrombin for the control of thrombosis is the N²-dansyl-L-arginine ester or amide. (Our pending U.S. application Ser. No. 496,939 filed Aug. 13, 1974, now U.S. Pat. No. 3,978,045.) However, there is a continuing need for a highly specific inhibitor on thrombin for the control of thrombosis, which exhibits lower toxicity.

SUMMARY OF THE INVENTION

It has now been discovered that N²-alkoxynaphthyl-sulfonyl-L-argininamides exhibit antithrombotic activity and even lower toxicity levels at the same relative potencies, as compared with the N²-dansyl-L-arginine ester or amide. The compounds of this invention can be represented by the formula (I):

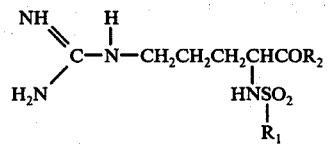

wherein $R_1$ is naphthyl substituted with at least one $C_1$–$C_5$ alkoxy; $R_2$ is piperidino substituted with —COOR$_3$ wherein $R_3$ is selected from the group consisting of hydrogen, $C_1$–$C_{10}$ alkyl, $C_6$–$C_{10}$ aryl, $C_7$–$C_{12}$ aralkyl and 5-indanyl, said substituted piperidino being optionally substituted with one or more substituents which, alike or different, may be $C_1$–$C_{10}$ alkyl, $C_1$–$C_{10}$ alkoxy, phenyl, alkoxycarbonyl or carboxy; and the —COOR$_3$ radical is at the 2 or 3-position of the piperidino radical.

Also encompassed within this invention are pharmaceutically acceptable salts thereof.

This invention also relates to a method for inhibiting activity and suppressing activation of thromin in vivo in mammals (antithrombotically) which comprises administering to a mammal a pharmaceutically effective amount of an N²-alkoxynaphthylsulfonyl-L-argininamide or the pharmaceutically acceptable salt thereof.

DETAILED DESCRIPTION OF THE PREFERRED EMBODIMENTS

This invention relates to a group of N²-alkoxynaphthylsulfonyl-L-argininamides of the formula (I):

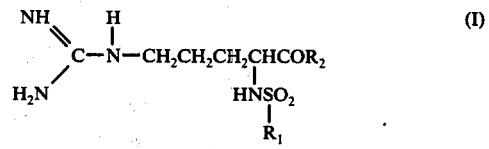

wherein $R_1$ is an alkoxynaphthyl wherein the alkoxy groups have 1–5 (preferably 1–3) carbon atoms, such as methoxy, ethoxy, propoxy, isopropoxy, butoxy, sec-butoxy, tert-butoxy, pentyloxy and the like, and preferred are those naphthyl groups having one or two alkoxy substituents, when two or more alkoxy groups are present, each may be the same or different; $R_2$ is piperidino substituted with —COOR$_3$ wherein $R_3$ is selected from the group consisting of hydrogen, alkyl of 1–10 carbon atoms, such as methyl, ethyl, propyl, butyl, tert-butyl, hexyl, octyl, decyl or the like, $C_6$–$C_{10}$ aryl such as phenyl, m-tolyl, p-tolyl, ethylphenyl, butylphenyl, naphthyl or the like, preferably phenyl and m-tolyl, aralkyl of 7–12 (preferably 7–10) carbon atoms, such as benzyl, phenethyl or the like, and 5-indanyl, said substituted piperidino being optionally substituted with one or more substituents which, alike or different, may be alkyl of 1–10 (preferably 1–6) carbon atoms, such as methyl, ethyl, propyl, butyl, hexyl octyl, decyl or the like, alkoxy of 1–10 (preferably 1–6) carbon atoms, such as methoxy, ethoxy, propoxy, isopropoxy, butoxy, isobutoxy, pentyloxy, ethylenedioxy, propylenedioxy or the like, phenyl or carboxy; and the —COOR$_3$ group is at the 2 or 3-position of the piperidino radical.

The suitable compounds of this invention can be represented by the formula (II):

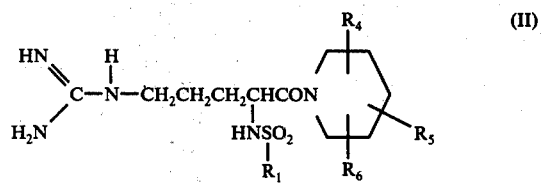

wherein $R_1$ is naphthyl substituted with at least one $C_1$–$C_5$ alkoxy; $R_4$ is —COOR$_3$ located at the 2 or 3-position, wherein $R_3$ is selected from the group consisting of hydrogen, $C_1$–$C_{10}$ alkyl, $C_6$–$C_{10}$ aryl, $C_7$–$C_{12}$ aralkyl and 5-indanyl; $R_5$ and $R_6$ are independently selected from the group consisting of hydrogen, $C_1$–$C_{10}$ alkyl, $C_1$–$C_{10}$ alkoxy, phenyl and carboxy, and $R_5$ and $R_6$ are the 2, 3, 4, 5 or 6-position of the piperidino radical.

Suitable illustrations of $R_1$ in the above formula (II) are 5-methoxy-1-naphthyl, 6-methoxy-2-napthyl, 7-methoxy-2-naphthyl, 4,6-dimethoxy-2-naphthyl, 6,7-dimethoxy-2-naphthyl and 6,7-diethoxy-2-naphthyl.

Suitable $R_3$ groups in the above formula (II) are hydrogen, methyl, ethyl, tert-butyl, octyl, phenyl, m-tolyl, benzyl and 5-indanyl.

Suitable $R_5$ and $R_6$ groups in the above formula (II) are hydrogen, methyl, ethyl, propyl, isopropyl, methoxy, ethoxy, phenyl and carboxy, and the suitable positions of $R_5$ and $R_6$ are 2, 4 and 6.

Illustrative of suitable $N^2$-alkoxynaphthylsulfonyl-L-argininamides of this invention are the following:

1-[$N^2$-(6,7-dimethoxy-2-naphthylsulfonyl)-L-arginyl]-2-piperidinecarboxylic acid Ethyl 1-[$N^2$-(6,7-dimethoxy-2-naphthylsulfonyl)-L-arginyl]-2-piperidinecarboxylate 1-[$N^2$-(6-methoxy-2-naphthylsulfonyl)-L-arginyl]-2-piperidinecarboxylic acid Ethyl 1-[$N^2$-(6-methoxy-2-naphthylsulfonyl)-L-arginyl]-2-piperidinecarboxylate 1-[$N^2$-(6,7-dimethoxy-2-naphthylsulfonyl)-L-aginyl]-4-methyl-2-piperidinecarboxylic acid 1-[$N^2$-(7-methoxy-2-naphthylsulfonyl)-L-arginyl]-4-methoxy-2-piperidinecarboxylic acid Ethyl 1-[$N^2$-(7-methoxy-2-naphthylsulfonyl)-L-arginyl]-4-methyl-2-piperidinecarboxylate 1-[$N^2$-(5-methoxy-1-naphthylsulfonyl)-L-arginyl]-4-methyl-2-piperidinecarboxylic acid Ethyl 1-[$N^2$-(5-methoxy-1-naphthylsulfonyl)-L-arginyl]-4-methyl-2-piperidinecarboxylate 1-[$N^2$-(4,6-dimethoxy-2-naphthylsulfonyl)-L-arginyl]-4-methyl-2-piperidinecarboxylic acid Ethyl 1-[$N^2$-(4,6-dimethoxy-2-naphthylsulfonyl)-L-arginyl]-4-methyl-2-piperidinecarboxylate 1-[$N^2$-(6,7-diethoxy-2-naphthylsulfonyl)-L-arginyl]-4-methyl-2-piperidinecarboxylic acid Ethyl 1-[$N^2$-(6,7-diethoxy-2-naphthylsulfonyl)-L-arginyl]-4-methyl-2-piperidinecarboxylate 1-[$N^2$-(6,7-dimethoxy-2-naphthylsulfonyl)-L-arginyl]-4-ethyl-2-piperidinecarboxylic acid Ethyl 1-[$N^2$-(6,7-dimethoxy-2-naphthylsulfonyl)-L-arginyl]-4-ethyl-2-piperidinecarboxylate 1-[$N^2$-(7-methoxy-2-naphthylsulfonyl)-L-arginyl]-4-ethyl-2-piperidinecarboxylic acid Ethyl 1-[$N^2$-(7-methoxy-2-naphthylsulfonyl)-L-arginyl]-4-ethyl-2-piperidinecarboxylate 1-[$N^2$-(6,7-dimethoxy-2-naphthylsulfonyl)-L-arginyl]-4-propyl-2-piperidinecarboxylic acid Ethyl 1-[$N^2$-(6,7-dimethoxy-2-naphthylsulfonyl)-L-arginyl]-4-propyl-2-piperidinecarboxylate 1-[$N^2$-(6,7-dimethoxy-2-naphthylsulfonyl)-L-arginyl]-4-isopropyl-2-piperidinecarboxylic acid Ethyl 1-[$N^2$-(6,7-dimethoxy-2-naphthylsulfonyl)-L-arginyl]-4-isopropyl-2-piperidinecarboxylate 1-[$N^2$-(6,7-dimethoxy-2-naphthylsulfonyl)-L-arginyl]-6-methyl-2-piperidinecarboxylic acid Ethyl 1-[$N^2$-(6,7-dimethoxy-2-naphthylsulfonyl)-L-arginyl]-6-methyl-2-piperidinecarboxylate 1-[$N^2$-(7-methoxy-2-naphthylsulfonyl)-L-arginyl]-2-methyl-2-piperidinecarboxylic acid Ethyl 1-[$N^2$-(7-methoxy-2-naphthylsulfonyl)-L-arginyl]-2-methyl-2-piperidinecarboxylate 1-[$N^2$-(6,7-dimethoxy-2-naphthylsulfonyl)-L-arginyl]-3-piperidinecarboxylic acid Methyl 1-[$N^2$-(6,7-dimethoxy-2-naphthylsulfonyl)-L-arginyl]-3-piperidinecarboxylate 1-[$N^2$-(7-methoxy-2-naphthylsulfonyl)-L-arginyl]-3-piperidinecarboxylic acid 1-[$N^2$-(7-methoxy-2-naphthylsulfonyl)-L-arginyl]-2,6-piperidinecarboxylic acid 1-[$N^2$-(6,7-dimethoxy-2-naphthylsulfonyl)-L-arginyl]-4-phenyl-2-piperidinecarboxylic acid Of the compounds of this invention, the following compounds are most preferred due to their high antithrombotic activity and low level of toxicity.

1-[$N^2$-(6,7-dimethoxy-2-naphthylsulfonyl)-L-arginyl]-4-methyl-2-piperidinecarboxylic acid 1-[$N^2$-(7-methoxy-2-naphthylsulfonyl)-L-arginyl]-4-methyl-2-piperidinecarboxylic acid 1-[$N^2$-(4,6-dimethoxy-2-naphthylsulfonyl)-L-arginyl]-4-methyl-2-piperidinecarboxylic acid 1-[$N^2$-(6,7-dimethoxy-2-naphthylsulfonyl)-L-arginyl]-4-ethyl-2-piperidinecarboxylic acid 1-[$N^2$-(7-methoxy-2-naphthylsulfonyl)-L-arginyl]-4-ethyl-2-piperidinecarboxylic acid 1-[$N^2$-(6,7-dimethoxy-2-naphthylsulfonyl)-L-arginyl]-4-propyl-2-piperidinecarboxylic acid The pharmaceutically acceptable salts of the above compounds are of course also included within the scope of this invention. The above compounds are intended only to illustrate the variety of structures which can be used in the process of this invention, and the above listing is not to be construed as limiting the scope of the invention. These typical compounds are highly potent in their antithrombotic activity. For the preparation of the compounds of this invention, various methods can be employed depending upon the particular starting materials and/or intermediates involved. Successful preparation of these compounds is possible by way of several synthetic routes which are outlined below.

a. Condensation of an L-argininamide with an alkoxynaphthalenesulfonyl halide This process may be illustrated as follows:

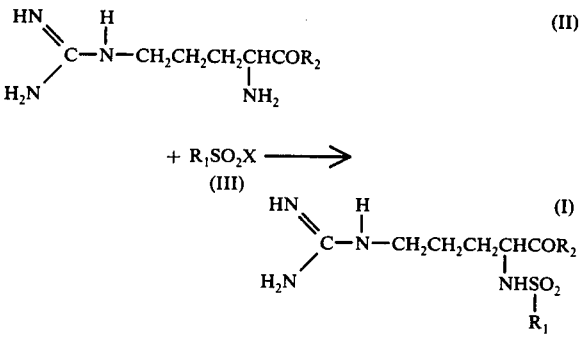

In the above formulas, $R_1$ and $R_2$ are as defined herein above, and X is halogen.

The $N^2$-alkoxynaphthylsulfonyl-L-argininamide (I) is prepared by the condensation of an L-argininamide (II) with a substantially equimolar amount of an alkoxynaphthalenesulfonyl halide (III), preferably a chloride.

The condensation reaction is generally effected in a suitable reaction-inert solvent in the presence of an excess of a base, such as an organic base (triethylamine, pyridine) or a solution of an inorganic base (sodium hydroxide, potassium carbonate), at a temperature of 0° C to the boiling temperature of the solvent for a period of 10 minutes to 15 hours.

The preferred solvents for the condensation include benzene-diethyl ether, diethyl ether-water and dioxane-water.

After the reaction is complete, the formed salt is extracted with water, and the solvent is removed by such standard means as evaporation under reduced pressure to give the $N^2$-alkoxynaphthylsulfonyl-L-argininamide (I), which can be purified by trituration or recrystallization from a suitable solvent, such as diethyl ether-tetrahydrofuran, diethyl ether-methanol and water-methanol, or may be chromatographed on silica gel.

The L-argininamides (II) starting materials required for the condensation reaction can be prepared by protecting the guanidino and α-amino groups of the L-arginine via nitration, acetylation, formylation, phthaloylation, trifluoroacetylation, p-methoxybenzyloxycarbonylation, benzoylation, benzyloxycarbonylation, tert-butoxycarbonylation or tritylation and then condensing the formed $N^G$-substituted-$N^2$-substituted-L-arginine with a corresponding piperidinecarboxylic acid or ester thereof by such a conventional process as the acid chloride method, azide method, mixed anhydride method, activated ester method or carbodiimide method, and thereafter selectively removing the protective groups.

In accordance with the process employed for preparing a 2-piperidinecarboxylic acid or an ester thereof, the following scheme is illustrative:

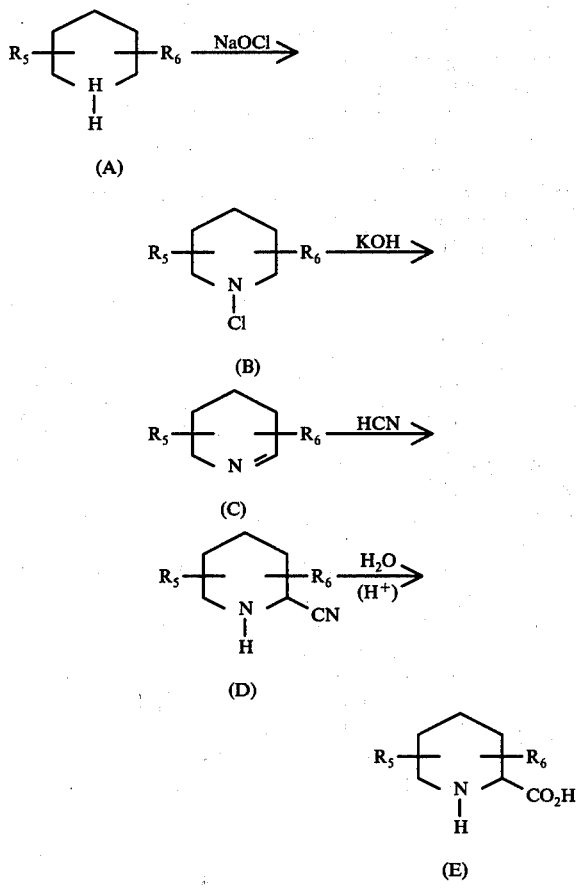

In the first reaction of the aforementioned scheme, an appropriately substituted piperidine (A) is contacted with an aqueous sodium hypochlorite solution at a temperature of −5° C to 0° C. The resultant product (B) is isolated by extraction with a solvent, e.g., diethyl ether, and then treated with potassium hydroxide in a lower alkanol solvent to give th 1,2-dehydropiperidine (C). The action of cyanogenating agents, e.g., hydrogen cyanide or sodium cyanide converts the 1,2-dehydropiperidines (C) to the corresponding 2-cyano analogs (D). Hydrolysis of the 2-cyanopiperidines (D) to yield the 2-piperidinecarboxylic acids (E) is effected by treatment of the 2-cyanopiperidines (D) with an inorganic acid, such as hydorchloric acid or sulfuric acid. The alkoxynaphthalenesulfonyl halides (III) which are the starting materials for the preparation of the $N^2$-alkoxynaphthylsulfonyl-L-argininamides (I) can be prepared by halogenating the requisite alkoxynaphthalenesulfonic acids or their salts, e.g., sodium salts, by conventional methods well known to those skilled in the art.

In practice, halogenation is carried out without a solvent or in a suitable solvent e.g., halogenated hydrocarbons or DMF in the presence of a halogenating agent, e.g., phosphorous oxychloride, thionyl chloride, phosphorous trichloride, phosphorous tribromide or phosphorous pentachloride, at a temperature of −10° to 200° C for a period of 5 minutes to 5 hours. After the reaction is complete, the reaction product is poured into ice water and then extracted with a solvent such as ether, benzene, ethyl acetate, chloroform or the like.

The alkoxynaphthalenesulfonyl halide can be purified by recrystallization from a suitable solvent such as hexane, benzene or the like.

(b) Removal of the $N^G$-substituent from an $N^G$-substituted-$N^2$-alkoxynaphthylsulfonyl-L-argininamide This process may be illustrated as follows:

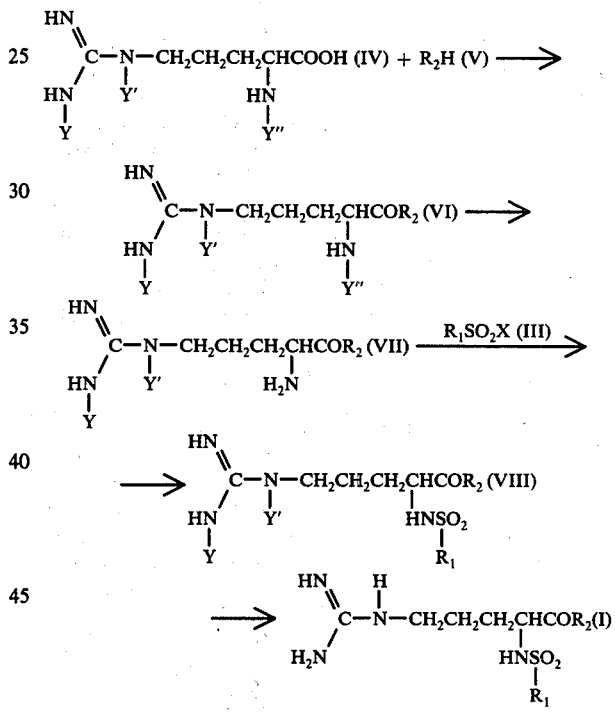

In the above formulas, $R_1, R_2$ and X are as defined herein above; Y''' is a protective group for the amino group, such as benzyloxycarbonyl or tert-butyoxycarbonyl; and Y and Y' are hydrogen and protective groups for the guanidino group, such as nitro, tosyl trityl, oxycarbonyl or the like. At least one of Y and Y' is a protective group for the guanidino group. The $N^2$-alkoxynaphthyl-sulfonyl-L-argininamide (I) is prepared by removing the $N^G$-substituent from an $N^G$-substituted-$N^2$-alkoxynaphthylsulfonyl-L-argininamide (VIII) by means of acidolysis or hydrogenolysis. The acidolysis is generally effected by contacting the $N^G$-substituted-$N^2$-alkoxynaphthylsulfonyl-L-argininamide (VIII) and an excess of an acid such as hydrogen fluoride, hydrogen chloride, hydrogen bromide or trifluoroacetic acid, without a solvent or in a solvent, such as an ether (tetrahydrofuran, dioxane), an alcohol (methanol, ethanol) or acetic acid at a temperature of −10° C to 100° C, and preferably at room temperature for a period of 30 minutes to 24 hours. The products are isolated by evaporation of the solvent and the excess acid, or by trituration with a suitable solvent followed by filtration and drying.

Because of the use of the excess acid, the products are generally the acid addition salts of the $N^2$-alkoxynaphthylsulfonyl-L-argininamides (I), which can be easily converted to a free amide by neutralization. The removal of the nitro group and the oxycarbonyl group, e.g., benzyloxycarbonyl, p-nitrobenzyloxycarbonyl, is readily accomplished by the hydrogenolysis.

The hydrogenolysis is effected in a reaction-inert solvent, e.g., methanol, ethanol, tetrahydrofuran or dioxane, in the presence of a hydrogen-activating catalyst, e.g., Raney nickel, palladium, or platinum, in a hydrogen atmosphere at a temperature of 0° C to the boiling temperature of the solvent for a period of 2 hours to 120 hours.

The hydrogen pressure is not critical, and atmospheric pressure is sufficient.

The $N^2$-alkoxynaphthylsulfonyl-L-argininamides (I) are isolated by filtration of the catalyst followed by evaporation of the solvent.

The $N^2$-alkoxynaphthylsulfonyl-L-argininamides can be purified in the same manner as described above.

The $N^G$-substituted-$N^2$-alkoxynaphthylsulfonyl-L-argininamides (VIII) starting materials can be prepared by condensing an $N^G$-substituted-$N^2$-substituted L-arginine (IV) (generally the $N^2$-substituent is a protective group for the amino group, such as benzyloxycarbonyl, tert-butoxycarbonyl, or the like) and a corresponding piperidinecarboxylic acid or ester thereof (V) via the azide method, mixed anhydride method, activated ester method, carbodiimido method or the like, selectively removing only the $N^2$-substituent of an $N^G$-substituted-$N^2$-substituted L-argininamide (VI) by means of catalytic hydrogenolysis or acidolysis, and then condensing the thus obtained $N^G$-substituted-L-argininamide (VII) with an alkoxynaphthalenesulfonyl Halide (III), preferably a chloride in the presence of a base in a solvent. These reaction conditions are as described above in the condensation of an L-argininamide with an alkoxynaphthalenesulfonyl halide, and the removal of the $N^G$-substituent from an $N^G$-substituted-$N^2$-alkoxy-napthylsulfonyl-L-argininamide.

(c) Condensation of an $N^2$-alkoxynaphthylsulfonyl-L-arginyl halide with a piperidinecarboxylic acid or an ester thereof This process may be illustrated as follows:

with at least an equimolar amount of a piperidinecarboxylic acid or an ester thereof (V).

The condensation reaction can be carried out without an added solvent. However, satisfactory results will be obtained with the use of a solvent such as basic solvents (dimethylformamide, dimethylacetamide, etc.) or halogenated solvents (chloroform, dichloromethane, etc.).

The amount of the solvent to be used is not critical and may vary from about 5 to 100 times the weight of the $N^2$-alkoxynaphthylsulfonyl-L-arginyl halide (IX). Preferred condensation reaction temperatures are in the range of from −10° C to room temperature. The reaction time is not critical, but varies with the piperidinecarboxylic acid or the ester thereof (V) employed. In general, a period of from 5 minutes to 10 hours is operable.

The obtained $N^2$-alkoxynaphthylsulfonyl-L-argininamide can be isolated and purified in the same manner as described above.

The $N^2$-alkoxynapththylsulfonyl-L-arginyl halide (IX) starting materials required for the condensation reaction can be prepared by reacting an $N^2$-alkoxynaphthylsulfonyl-L-arginine with at least an equimolar amount of a halogenating agent such as thionyl chloride, phosphorous oxychloride, phosphorus trichloride, phosphorous pentachloride or phosphorus tribromide. The halogenation can be carried out with or without an added solvent.

The preferred solvents are chlorinated hydrocarbons such as chloroform and dichloromethane, and ethers such as tetrahydrofuran and dioxane.

The amount of the solvent to be used is not critical and may vary from about 5 to 100 times the weight of the $N^2$-alkoxynaphthylsulfonyl-L-arginine. Preferred reaction temperatures are in the range of −10° C to room temperature. The reaction time is not critical, but varies with the halogenating agent and reaction temperature. In general, a period of 15 minutes to 5 hours is operable.

The $N^2$-alkoxynaphthylsulfonyl-L-arginines which are the starting materials for the preparation of the $N^2$-alkoxynaphthylsulfonyl-L-arginyl halides can be prepared by the condensation of L-arginine with a substantially equimolar amount of alkoxynaphthalenesulfonyl halides, by a method similar to that described in the condensation of an L-argininamide with an alkoxynaphthalenesulfonyl halide.

(d) Guanidylation of an $N^2$-alkoxynaphthylsulfonyl-L-ornithinamide or an acid addition salt thereof. This process may be illustrated as follows:

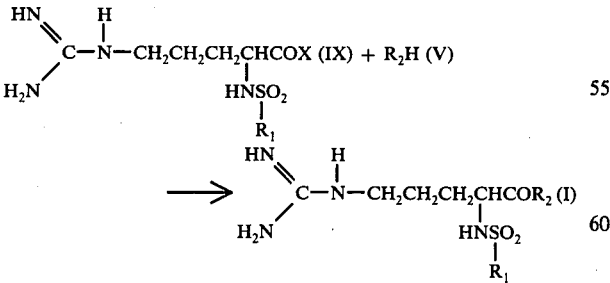

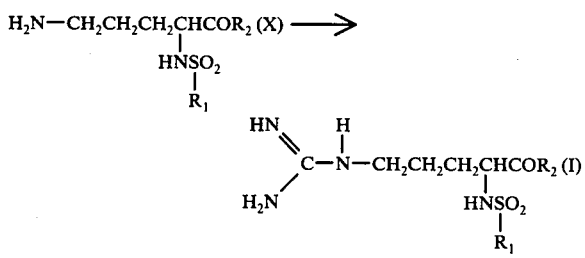

In the above formulas, $R_1$, $R_2$ and X are defined herein above.

The $N^2$-alkoxynapthylsulfonyl-L-argininamide (I) is prepared by the condensation of an $N^2$-alkoxynapthylsulfonyl-L-arginyl halide (IX), preferably a chloride In the above formulas, $R_1$ and $R_2$ are as defined herein above.

The $N^2$-alkoxynaphthylsulfonyl-L-argininamide (I) is prepared by guanidylating an $N^2$-alkoxynaphthylsulfonyl-L-ornithinamide (X) with an ordinary guanidylating such as an O-alkylisourea, S-alkylisothiourea, 1-guanyl-3,5-dimethylpyrazole or carbodiimide. The preferred guanidylating agents are the O-alkylisourea and the S-alkylisothiourea.

The guanidylation of the $N^2$-alkoxynaphthylsulfonyl-L-ornithinamide (X) with the O-alkylisourea or S-alkylisothiourea is generally effected in a solvent in the presence of a base at a temperature of from 0° C to the boiling temperature of the solvent for a period of from 30 minutes to 50 hours.

Examples of preferred base are triethylamine, pyridine, sodium hydroxide and sodium methoxide. The base is used in an amount of 0.01 to 0.1 equivalent to the $N^2$-alkoxynaphthylsulfonyl-L-ornithinamide.

Examples of the preferred solvents are water, water-ethanol and water-dioxane.

After the reaction is complete, the $N^2$-alkoxynaphthylsulfonyl-L-argininamide (I) is isolated by evaporation of the solvent followed by removal of the excess base and the formed salt by a water wash.

It is well recognized in the art that an ester derivative of the $N^2$-alkoxynaphthylsulfonyl-L-argininamide (I) wherein $R_3$ is alkyl, aryl, aralkyl, or 5-indanyl, can be prepared from a carboxylic acid derivative of the $N^2$-alkoxynaphthylsulfonyl-L-argininamide wherein $R_4$ is hydrogen, by the conventional esterification methods well known to those skilled in the art. It is also well recognized in the art that the carboxylic acid derivative can be prepared from the ester derivative by the conventional hydrolysis or acidolysis methods. The conditions under which esterification, hydrolysis or acidolysis would be carried out will be each apparent to those skilled in the art.

The $N^2$-alkoxynaphthylsulfonyl-L-argininamide (I) of this invention forms acid addition salts with any of a variety of inorganic and organic acids. Some of the $N^2$-alkoxynaphthylsulfonyl-L-argininamide containing a free carboxy group, wherein $R_3$ is hydrogen, forms salts with any of a variety of inorganic and organic bases. The product of the reactions described above can be isolated in the free form or in the form of salts. In addition, the product can be obtained as pharmaceutically acceptable acid addition salts by reacting one of the free bases with an acid, such as hydrochloric, hydrobromic, hydroiodic, nitric, sulfuric, phosphoric, acetic, citric, maleic, succinic, lactic, tartaric, gluconic, benzoic, methanesulfonic, ethanesulfonic, benzenesulfonic, p-toluenesulfonic acid or the like. In a similar manner, the product can be obtained as pharmaceutically acceptable salts by reacting one of the free carboxylic acids with a base, such as sodium hydroxide, potassium hydroxide, ammonium hydroxide, triethylamine, procaine, dibenzylamine, 1-ephenamine, N,N'-dibenzylethylenediamine, N-ethylpiperidine or the like.

Likewise, treatment of the salts with a base or acid results in a regeneration of the free amide.

As stated above, the $N^2$-alkoxynaphthylsulfonyl-L-argininamides, and the salts thereof of this invention are characterized by highly specific inhibitory activity in mammals against thrombin as well as their substantial lack of toxicity, and therefore these compounds are useful in the determination of thrombin in blood as diagnostic reagents, and/or for the medical control or prevention of thrombosis.

The antithrombotic activities of the $N^2$-alkoxynaphthylsulfonyl-L-argininamide of this invention were compared with that of a known antithrombotic agent, $N^2$-(p-tolylsulfonyl)-L-arginine methyl ester, by determining the fibrinogen coagulation time. The measurement of the fibrinogen coagulation time was conducted as follows:

An 0.8 ml aliquot of a fibrinogen solution, which had been prepared by dissolving 150 mg of bovine fibrinogen (Cohn fraction I) supplied by Armour Inc. in 40 ml of a borate saline buffer (pH 7.4), was mixed with 0.1 ml of a borate saline buffer, pH 7.4, (control) or a sample solution in the same buffer, and 0.1 ml of a thrombin solution (5 units/ml) supplied by Mochida Pharmaceutical Co., Ltd. was added to the solutions in an ice bath. Immediately after mixing, the reaction mixture was transferred from the ice bath to a bath maintained at 25° C. Coagulation times were taken as the period between the time of transference to the 25° C bath and the time of the first appearance of fibrin threads. In the cases where no drug samples were added, the coagulation time was 50-55 seconds.

The experimental results are summarized in Table 1. The term "concentration required to prolong the coagulation time by a factor of two" is the concentration of an active ingredient required to prolong the normal coagulation time 50-55 seconds to 100-110 seconds.

The concentration required to prolong the coagulation time by a factor of two for the known antithrombotic agent, $N^2$-(p-tolylsulfonyl)-L-arginine methyl ester, was 1,100μM. The inhibitors are shown in Table 1 by indicating $R_1$ and $R_2$ in the formula (I) and the addition moiety.

When a solution containing an $N^2$-alkoxynaphthylsulfonyl-L-argininamide of this invention was administered intravenously into animal bodies, the high antithrombotic activity in the circulating blood was maintained for from one to three hours. The halflife for decay of the antithrombotic compounds of this invention in circulating blood was shown to be approximately 60 minutes; the physiological conditions of the host animals (mammals such as rat, rabbit, dog and chimpanzee) were well maintained. The experimental decrease of fibrinogen in animals caused by infusion of thrombin was satisfactorily controlled by simultaneous infusion of the compounds of this invention.

The acute toxicity values ($LD_{50}$) determined by intraperitoneal administration of substances of formula (I) in mice (male, 20 g) range from about 1,000 to 10,000 milligrams per kilogram of body weight. Representative $LD_{50}$ values, for example, for 1-[$N^2$-(6,7-dimethoxy-2-naphthylsulfonyl)-L-arginyl]-2-piperidinecarboxylic acid, Ethyl 1-[$N^2$-(7-methoxy-2-naphthylsulfonyl)-L-arginyl]-4-methyl-2-piperidinecarboxylate and 1-[$N^2$-(4,6-dimethoxy-2-naphthylsulfonyl)-L-arginyl]-4-methyl-2-piperidinecarboxylic acid are 1,500, 670-1,000 and 670-1,000 milligrams per kilogram, respectively. On the other hand, $LD_{50}$ values for $N^2$-dansyl-N-butyl-L-argininamide and $N^2$-dansyl-N-methyl-N-butyl-L-argininamide are 75 and 70 milligrams per kilogram, respectively. The therapeutic agents of this invention may be administered to mammals including humans, alone or in combination with pharmaceutically acceptable carriers, the proportion of which is determined by the solubility and chemical nature of the compound, chosen route of administration and standard pharmaceutical practice. For example, the compounds may be injected parenterally, that is, intramuscularly, intravenously or subcutaneously. For parenteral administration, the compounds may be used in the form of sterile solutions containing other solutes, for example, sufficient saline or glucose to make the solution isotonic. The compounds may be administered orally in the form of tablets, capsules, or granules containing suitable excipients such as starch, lactose, white sugar and the like. The compounds may be administered sublingually in the form of troches or lozenges in which each active ingredient is mixed with sugar or corn syrups, flavoring agents and dyes, and then dehydrated sufficiently to make the mixture suitable for pressing into solid form. The compounds may be administered orally in the form of solutions which may contain coloring and flavoring agents.

Physicians will determine the dosage of the present therapeutic agents which will be most suitable for humans, and dosages vary with the mode of administration and the particular compound chosen. In addition, the dosage will vary with the particular patient under treatment.

When the composition is administered orally, a larger quantity of the active agent will be required to produce the same effect as caused with a smaller quantity given parenterally. The therapeutic dosage is generally 10–50 mg/kg of active ingredient parenterally, 10–500 mg/kg orally per day.

Having generally described the invention, a more complete understanding can be obtained by reference to certain specific examples, which are included for purposes of illustration only and are not intended to be limiting unless otherwise specified.

EXAMPLE 1

(A) Benzyl 1-[$N^G$-nitro-$N^2$-(6,7-dimethoxy-2-naphthylsulfonyl)-L-arginyl]-4-methyl-2-piperidinecarboxylate To a well stirred solution of 3.0 g of benzyl 1-($N^G$-nitro-L-arginyl)-4-methyl-2-piperidinecarboxylate hydrochloride and 1.4 g of $K_2CO_3$ in 15 ml of water and 40 ml of dioxane, was added in portions 2.87 g of 6,7-dimethoxy-2-naphthalenesulfonyl chloride, while maintaining the temperature at 0° C. The reaction mixture was stirred overnight at room temperature. At the end of this period, the reaction mixture was evaporated to dryness. The residue was taken up in 50 ml of chloroform, and the chloroform solution was washed consecutively with 10% citric acid, saturated NaCl, saturated $NaHCO_3$ and saturated NaCl solutions. The chloroform solution was evaporated and the residue was chromatographed on silica gel packed in chloroform, and eluted from chloroform containing 3% ethanol. The main fraction was evaporated to dryness to give 1.0 g of benzyl 1-[$N^G$-nitro-$N^2$-(6,7-dimethoxy-2-naphthylsulfonyl)-L-arginyl]-4-methyl-2-piperidinecarboxylate.

(B) 1-[$N^2$-(6,7-dimethoxy-2-naphthylsulfonyl)-L-arginyl]-4-methyl-2-piperidinecarboxylic acid.

To a solution of 0.7 g of benzyl 1-[$N^G$-nitro-$N^2$-(6,7-dimethoxy-2-naphthylsulfonyl)-L-arginyl]-4-methyl-2-piperidinecarboxylate in 10 ml of tert-butanol, 5 ml of water and 2 ml of acetic acid, was added 0.2 g of palladium black and then the mixture was shaken in a hydrogen atmosphere for 15 hours at room temperature. The solution was filtered to remove the catalyst and evaporated to give an oily product.

Reprecipitation with ethanol-diethyl ethyl gave 0.5 g of 1-[$N^2$-(6,7-dimethoxy-2-naphthylsulfonyl)-L-arginyl]-4-methyl-2-piperidinecarboxylic acid.

I.R. (KBr): 3,370, 1,625, 1,158 cm$^{-1}$

Analysis - Calcd. for $C_{25}H_{35}O_7N_5S$ (percent): C, 54.63; H, 6.42; N, 12.74 Found (percent): C, 54.50; H, 6.09; N, 12.81.

EXAMPLE 2

(A) $N^2$-(6-methoxy-2-naphthylsulfonyl)-L-arginyl chloride hydrochloride

A suspension of 2.5 g of $N^2$-(6-methoxy-2-naphthylsulfonyl)-L-arginine in 20 ml of thionyl chloride was stirred for 2 hours at room temperature. Addition of cold dry diethyl ether resulted in a precipitate which was collected by filtration and washed several times with dry diethyl ether to give $N^2$-(6-methoxy-2-naphthylsulfonyl)-L-arginyl chloride hydrochloride.

(B) Ethyl 1-[$N^2$-(6-methoxy-2-naphthylsulfonyl)-L-arginyl]-2-piperidinecarboxylate To a stirred solution of 2.2 of ethyl 2-piperidinecarboxylate and 4.1 ml of triethylamine in 50 ml of chloroform, which was cooled in an ice-salt bath, was added in portions $N^2$-(6-methoxy-2-naphthylsulfonyl)-L-arginyl chloride hydrochloride obtained above. The reaction mixture was stirred overnight at room temperature. At the end of this period, 500 ml of chloroform was added and the chloroform solution was washed twice with 50 ml of saturated sodium chloride solution, dried over anhydrous sodium sulfate and evaporated in vacuo. The oily residue was washed with ether to give 2.9 g of powdery ethyl 1-[$N^2$-(6-methoxy-2-naphthylsulfonyl)-L-arginyl]-2piperidinecarboxylate. For analysis of the product, a portion of the product was converted to the flavianate, M.P. 192°–3° C.

I.R. (KBr): 3,210, 1,747, 1,638 cm$^{-1}$

Analysis - Calcd. for $C_{25}H_{35}O_6N_5S.C_{10}H_6O_8N_2S$ (percent): C, 49.58; H, 4.87; N, 11.56 Found (percent): C, 49.24; H, 4.70; N, 11.85.

(C) 1-[$N^2$-(6-methoxy-2-naphthylsulfonyl)-L-arginyl]-2-piperidinecarboxylic acid A solution of 2.8 g of ethyl 1-[$N^2$-(6-methoxy-2-naphthylsulfonyl)-L-arginyl]-2-piperidinecarboxylate in 15 ml of methanol and 10 ml of 2N-NaOH solution was warmed to 60° C and held at that temperature for 10 hours. At the end of this period, the reaction mixture was concentrated and chromatographed on 200 ml of Daiaion ® SK 102 ion exchange resin (200–300 mesh, H$^+$ form, manufactured by Mitsubishi Chemical Industries Limited) packed in water, washed with ethanol-water (1:4) and eluted with ethanol-water-NH$_4$OH (10:9:1). The main fraction was evaporated to dryness and washed with ether to give 2.0 g of 1-[$N^2$-(6-methoxy-2-naphthylsulfonyl)-L-arginyl]-2-piperidinecarboxylic acid as an amorphous solid.

I.R. (KBr): 3,200 (broad), 1,620, 1,150 cm$^{-1}$

Analysis — Calcd. for $C_{23}H_{31}O_6N_5S$ (percent): C, 54.64; H, 6.18; N, 13.85 Found (percent): C, 56.88; H, 6.31; N, 13.83

Various other $N^2$-alkoxynaphthylsulfonyl-L-argininamides or acid addition salts thereof were synthesized in accordance with the procedure of the above examples, and the test results are summarized in Table 1.

Table 1

| Sample No. | Compound $HN\underset{H_2N}{\overset{HN}{=}}C-\underset{H}{N}-CH_2CH_2CH_2\underset{\underset{R_1}{\mid}}{CH}COR_2$ | | Addition moiety | Concentration required to prolong the coagulation time by a factor of two (μM) | Preparation process (Ex. No.) | m.p. (°C) | Elementary analysis Upper: Calculated Lower: Found | | | I.R. (KBr) (cm$^{-1}$) |
|---|---|---|---|---|---|---|---|---|---|---|
| | $R_1$ | $R_2$ | | | | | C | H | N | |
| 1 | 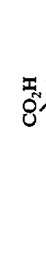 |  | — | | 2 | powder | 55.40<br>55.65 | 6.62<br>6.81 | 12.43<br>12.19 | 3,220<br>1,750<br>1,640 |
| 2 | " | 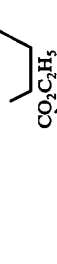 | — | 5 | " | powder | 53.82<br>53.66 | 6.21<br>5.96 | 13.08<br>12.81 | 3,350<br>1,625<br>1,155 |
| 3 |  | 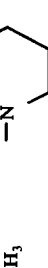 | 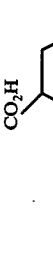 | | " | 192–193° C | 49.58<br>49.24 | 4.87<br>4.70 | 11.56<br>11.85 | 3,210<br>1,747<br>1,638 |
| 4 | " | " | — | 3 | " | powder | 54.64<br>56.88 | 6.18<br>6.31 | 13.85<br>13.83 | 3,200(broad)<br>1,620<br>1,150 |
| 5 | 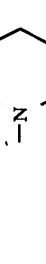 | 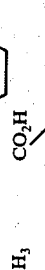 | — | 0.4 | 1 | powder | 54.63<br>54.50 | 6.42<br>6.09 | 12.74<br>12.81 | 3,370<br>1,625<br>1,158 |
| 6 | " | " |  | | 2 | 188–190° C | 50.17<br>50.01 | 5.03<br>4.78 | 11.38<br>11.56 | 3,200<br>1,740<br>1,635 |
| 7 | " | " | — | 0.15 | 2 | powder | 55.47<br>55.49 | 6.40<br>6.33 | 13.98<br>13.51 | 3,250(broad)<br>1,625 |

Table 1-continued

| Sample No. | Compound $HN=C(NH_2)-N(H)-CH_2CH_2CH_2CHCOR_2 / HNSO_2R_1$ | | Addition moiety | Concentration required to prolong the coagulation time by a factor of two (μM) | Preparation process (Ex. No.) | m.p. (°C) | Elementary analysis Upper: Calculated Lower: Found | | | I.R. (KBr) (cm$^{-1}$) |
|---|---|---|---|---|---|---|---|---|---|---|
| | $R_1$ | $R_2$ | | | | | C | H | N | |
| 8 | 5-methyl-1-methoxynaphthyl | 2-CO$_2$C$_2$H$_5$, 4-CH$_3$ piperidinyl | — | | " | powder | 57.02 56.81 | 6.81 6.91 | 12.79 12.78 | 3,200 1,740 1,635 |
| 9 | " | 2-CO$_2$H, 4-CH$_3$ piperidinyl | — | | " | powder | 55.47 55.31 | 6.40 6.68 | 13.48 13.21 | 3,350 1,620 1,150 |
| 10 | 3-methyl-5,8-dimethoxynaphthyl | 2-CO$_2$C$_2$H$_5$, 4-CH$_3$ piperidinyl | HO$_3$S-naphthyl(OH)(NO$_2$)$_2$ | | " | 222–3° C | 49.82 49.57 | 5.09 4.88 | 11.99 11.68 | 3,200 1,745 1,630 |
| 11 | 3-methyl-5,8-dimethoxynaphthyl | 2-CO$_2$H, 4-CH$_3$ piperidinyl | — | 0.35 | " | powder | 54.63 54.55 | 6.42 6.42 | 12.74 12.58 | 3,350(broad) 1,620 1,150 |
| 12 | 6-methyl-2,3-diethoxynaphthyl | 2-CO$_2$C$_2$H$_5$, 4-CH$_3$ piperidinyl | HO$_3$S-naphthyl(OH)(NO$_2$)$_2$ | | " | 154–6° C | 50.92 51.28 | 5.37 5.21 | 10.66 10.59 | 3,400 1,735 1,635 |
| 13 | " | 2-CO$_2$H, 4-CH$_3$ piperidinyl | — | | " | powder | 56.13 56.11 | 6.80 6.85 | 12.12 11.95 | 3,300(broad) 1,610 1,255 |
| 14 | 6-methyl-2,3-dimethoxynaphthyl | 2-CO$_2$C$_2$H$_5$, 4-C$_2$H$_5$ piperidinyl | HO$_3$S-naphthyl(OH)(NO$_2$)$_2$ | | " | 179–180° C | 50.38 50.34 | 5.23 5.18 | 10.82 11.05 | 3,380 1,735 1,635 |

Table 1-continued

Compound structure:

$$HN=C(NH_2)-N(H)-CH_2CH_2CH_2CH(NHSO_2R_1)-COR_2$$

| Sample No. | $R_1$ | $R_2$ | Addition moiety | Concentration required to prolong the coagulation time by a factor of two (μM) | Preparation process (Ex. No.) | m.p. (° C) | Elementary analysis Upper: Calculated Lower: Found | | | I.R. (KBr) (cm$^{-1}$) |
|---|---|---|---|---|---|---|---|---|---|---|
| | | | | | | | C | H | N | |
| 15 | " | $CO_2H$, 4-$C_2H_5$-piperidyl | — | | " | powder | 55.40 / 55.71 | 6.62 / 6.48 | 12.43 / 12.53 | 3,360 / 1,620 / 1,150 |
| 16 | 6-OCH$_3$-naphthyl | $CO_2C_2H_5$, 4-$C_2H_5$-piperidyl | HO$_3$S—(naphthyl)—OH, NO$_2$, NO$_2$ | | " | 125 (soften) | 50.73 / 50.58 | 5.18 / 5.11 | 11.19 / 10.93 | 3,380 / 1,730 / 1,630 |
| 17 | " | $CO_2H$, 4-$C_2H_5$-piperidyl | — | | " | powder | 56.26 / 56.41 | 6.61 / 6.48 | 13.12 / 13.27 | 3,360 / 1,620 / 1,150 |
| 18 | 6,7-di-OCH$_3$-naphthyl | $CO_2C_2H_5$, 4-$CH_2CH_2CH_3$-piperidyl | — | | " | powder | 57.50 / 57.56 | 7.15 / 7.08 | 11.56 / 11.71 | 3,330 / 2,960 / 1,740 / 1,640 |
| 19 | " | $CO_2H$, 4-$CH_2CH_2CH_3$-piperidyl | — | 0.5 | " | powder | 56.13 / 56.11 | 6.80 / 6.81 | 12.12 / 11.96 | 3,400 / 1,620 |
| 20 | " | $CO_2C_2H_5$, 4-CH(CH$_3$)$_2$-piperidyl | — | | " | powder | 57.50 / 57.15 | 7.15 / 7.21 | 11.56 / 11.62 | 3,360 / 2,960 / 1,730 |
| 21 | " | $CO_2H$, 4-CH(CH$_3$)$_2$-piperidyl | — | | " | powder | 56.13 / 56.21 | 6.80 / 6.81 | 12.12 / 12.03 | 3,400 / 1,620 / 1,150 |

Table 1-continued

| Sample No. | Compound R₁ | R₂ | Addition moiety | Concentration required to prolong the coagulation time by a factor of two (μM) | Preparation process (Ex. No.) | m.p. (° C) | Elementary analysis Upper: Calculated Lower: Found | | | I.R. (KBr) (cm⁻¹) |
|---|---|---|---|---|---|---|---|---|---|---|
| | | | | | | | C | H | N | |
| 22 | " | piperidine-CO₂H | — | | | powder | 54.63 54.54 | 6.42 6.40 | 12.74 12.68 | 3,350 1,620 1,150 |
| 23 | " | piperidine with CO₂C₂H₅ and CH₃ | — | | | powder | 56.13 56.08 | 6.80 6.91 | 12.12 12.08 | 3,250 1,740 1,640 |
| 24 | " | piperidine with H₃C, CO₂C₂H₅ | — | | | powder | 57.02 56.86 | 6.81 6.83 | 12.79 12.68 | 3,230 1,740 1,650 |
| 25 | " | piperidine with H₃C, CO₂H | — | | | powder | 54.63 54.59 | 6.42 6.38 | 12.74 12.68 | 3,250 1,620 1,160 |
| 26 | OCH₃ (methoxynaphthyl) | piperidine-CO₂CH₃ | HO₃S-naphthol with OH, NO₂, NO₂ | | 2 | 161–163° C | 48.97 49.05 | 4.71 4.73 | 11.76 11.58 | 3,340 1,738 1,635 |
| 27 | OCH₃, OCH₃ (dimethoxynaphthyl) | piperidine-CO₂H | — | | 2 | powder | 53.82 53.68 | 6.21 6.08 | 13.08 12.85 | 3,370 1,635 1,255 1,155 |

Table 1-continued

Compound
$$HN\phantom{xx}H$$
$$\phantom{xx}\diagdown\phantom{xx}|$$
$$\phantom{xxx}C-N-CH_2CH_2CH_2CHCOR_2$$
$$H_2N\diagup\phantom{xxxxxxxxxxx}|$$
$$\phantom{xxxxxxxxxxxxxx}HNSO_2$$
$$\phantom{xxxxxxxxxxxxxxxxxx}|$$
$$\phantom{xxxxxxxxxxxxxxxxxx}R_1$$

| Sample No. | $R_1$ | $R_2$ | Addition moiety | Concentration required to prolong the coagulation time by a factor of two (μM) | Preparation process (Ex. No.) | m.p. (° C) | Elementary analysis Upper: Calculated Lower: Found | | | I.R. (KBr) (cm$^{-1}$) |
|---|---|---|---|---|---|---|---|---|---|---|
| | | | | | | | C | H | N | |
| 28 | 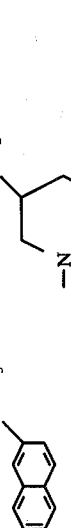 | 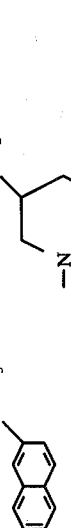 | — | | " | powder | 54.64<br>54.58 | 6.18<br>6.09 | 13.85<br>13.93 | 3,370<br>1,640<br>1,260<br>1,155 |
| 29 | " | | — | | " | powder | 48.55<br>48.31 | 4.93<br>4.64 | 11.80<br>11.53 | 3,300 (broad)<br>1,620 |
| 30 | 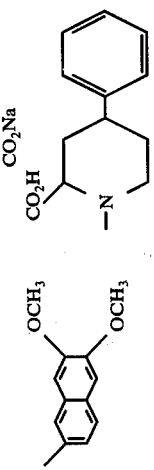 | | — | 12 | " | powder | 59.89<br>59.65 | 4.52<br>4.63 | 11.64<br>11.81 | 3,360<br>1,620<br>1,255<br>1,150 |

The following compounds are prepared in a similar manner:

1-[$N^2$-(5-methoxy-1-naphthylsulfonyl)-L-arginyl]-4-ethyl-2-piperidinecarboxylic acid
1-[$N^2$-(6-methoxy-2-naphthylsulfonyl)-L-arginyl]-4-ethyl-2-piperidinecarboxylic acid
1-[$N^2$-(4,6-dimethoxy-2-naphthylsulfonyl)-L-arginyl]-4-ethyl-2-piperidinecarboxylic acid
1-[$N^2$-(5-ethoxy-1-naphthylsulfonyl)-L-arginyl]-4-ethyl-2-piperidinecarboxylic acid
1-[$N^2$-(7-ethoxy-2-naphthylsulfonyl)-L-arginyl]-4-ethyl-2-piperidinecarboxylic acid
1-[$N^2$-(6,7-diethoxy-2-naphthylsulfonyl)-L-arginyl]-4-ethyl-2-piperidinecarboxylic acid
1-[$N^2$-(7-methoxy-2-naphthylsulfonyl)-L-arginyl]-4-tert-butyl-2-piperidinecarboxylic acid
Phenyl 1-[$N^2$-(7-methoxy-2-naphthylsulfonyl)-L-arginyl]-4-ethyl-2-piperidinecarboxylate
Benzyl 1-[$N^2$-(7-methoxy-2-naphthylsulfonyl)-L-arginyl]-4-ethyl-2-piperidinecarboxylate
Benzyl 1-[$N^2$-(6,7-dimethoxy-2-naphthylsulfonyl)-L-arginyl]-4-methyl-2-piperidinecarboxylate
1-[$N^2$-(6,7-dimethoxy-2-naphthylsulfonyl)-L-arginyl]-4-methoxy-2-piperidinecarboxylic acid
1-[$N^2$-(7-methoxy-2-naphthylsulfonyl)-L-arginyl]-4-methoxy-2-piperidinecarboxylic acid
1-[$N^2$-(6-methoxy-2-naphthylsulfonyl)-L-arginyl]-4-ethoxy-2-piperidinecarboxylic acid
1-[$N^2$-(6,7-dimethoxy-2-naphthylsulfonyl)-L-arginyl]-4-methyl-4-methoxy-2-piperidinecarboxylic acid
1-[$N^2$-(6,7-dimethoxy-2-naphthylsulfonyl)-L-arginyl]-4-propoxy-2-piperidinecarboxylic acid
1-[$N^2$-(6,7-dimethoxy-2-naphthylsulfonyl)-L-arginyl]-6-methoxy-2-piperidinecarboxylic acid

EXAMPLE 3

Tablets suitable for oral administration Tablets containing the ingredients indicated below may be prepared by conventional techniques.

| Ingredient | Amount per tablet (mg) |
| --- | --- |
| 1-[$N^2$-(6,7-dimethoxy-2-naphthylsulfonyl)-L-arginyl]-4-methyl-2-piperidinecarboxylic acid | 250 |
| Lactose | 140 |
| Corn starch | 35 |
| Talcum | 20 |
| Magnesium stearate | 5 |
| Total | 450 mg |

EXAMPLE 4

Capsules for oral administration

Capsules of the below were made up by throughly mixing together batches of the ingredients and filling hard gelatin capsules with the mixture.

| Ingredient | Amount per capsule (mg) |
| --- | --- |
| 1-[$N^2$-(7-methoxy-2-naphthylsulfonyl)-L-arginyl]-4-methyl-2-piperidinecarboxylic acid | 250 |
| Lactose | 250 |
| Total | 500 mg |

EXAMPLE 5

Sterile solution for infusion

The following ingredients are dissolved in water for intravenous perfusion and the resulting solution is then sterilized.

| Ingredients | Amount (g) |
| --- | --- |
| 1-[$N^2$-(6,7-dimethoxy-2-naphthylsulfonyl)-L-arginyl]-4-ethyl-2-piperidinecarboxylic acid | 0.25 |
| Buffer system | As desired |
| Glucose | 25 |
| Distilled water | 500 |

PREPARATION

2-Piperidinecarboxylic acids and esters thereof (A) 4-methyl-2-piperidinecarbonitrile To 500 g of 10% sodium hypochlorite solution cooled in an ice bath, there was added dropwise a solution of 33.6 g (0.21 mole) of 4-methylpiperidine acetate in 10 ml of water over a period of 1 hour. At the end of this period, the reaction product was extracted twice with 500 ml of ethyl ether and dried over anhydrous sodium sulfate. After evaporation of ethyl ether, the residue was added dropwise to a solution of 11.8 g (0.21 mole) of potassium hydroxide in 96% ethanol under reflux. Refluxing was continued for an additional 10 minutes. Ethanol was evaporated, and the residue was dissolved into 50 ml of 2N sodium hydroxide solution and then extracted with ether.

The ether layer was dried over anhydrous sodium sulfate and then ether evaporated. The residue was added to an ice-cooled solution of 27 g (1 mole) of hydrogen cyanide and 25 ml of concentrated hydrochloric acid in 300 ml of water. The solution was stirred at a temperature of 10° to 20° C for 4 hours and thereafter made basic by the addition of solid sodium hydroxide. The reaction product was extracted with ether, dried over anhydrous sodium sulfate and then distilled under reduced pressure to give 17 g (66%) of 4methyl-2-piperidinecarbonitrile, B.P. 96°–97° C/10 mmHg.

The following 2-piperidinecarbonitriles not previously reported in the chemical literature were synthesized by the aforementioned procedure which is essentially that as taught by Grundon et al., J. Chem. Soc., 1963, 3898, Grundon et al., J. Chem. Soc., 1964, 2448, R. Bonnett et al., J. Chem. Soc., 1959, 2092 and H. Bohme et al., Ber., 92 1613 (1959).

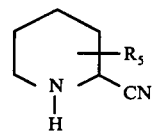

| No. | $R_5$ | B.P. |
| --- | --- | --- |
| 1 | 4-$CH_2CH_3$ | 105–106° C/9 mmHg. |
| 2 | 4-$CH_2CH_2CH_3$ | 116° C/8 mmHg. |
| 3 | 4-CH(CH$_3$)$_2$ | 104° C/4 mmHg. |
| 4 | 2-$CH_3$ | |

(B) 4-Methyl-2-piperidinecarboxylic acid hydrochloride

A solution of 16 g of 4-methyl-2-piperidinecarbonitrile in 250 ml of 6N hydrochloric acid was refluxed for 6 hours. After evaporation of the solvent, the residue was recrystallized from water to give 13 g of 4-methyl-2-piperidinecarboxylic acid hydrochloride.

(C) Ethyl 4-methyl-2-piperidinecarboxylate

A solution of 13 g (0.072 mole) of 4-methyl-2-piperidinecarboxylic acid hydrochloride and 50 ml of thionyl chloride in 300 ml of ethanol was refluxed for 4 hours. At the end of this period, the solvent was evaporated under reduced pressure, and the residue was extracted with a solution of chloroform and saturated potassium carbonate solution.

The chloroform layer was dried over anhydrous sodium sulfate and then chloroform was evaporated. Distillation of the residue gave 7.4 g (60%) of ethyl 4-methyl-2-piperidinecarboxylate, B.P. 76°–77° C/3 mmHg.

(D) Benzyl 4-methyl-2-piperidinecarboxylate p-toluenesulfonate A solution of 20 g (0.112 mole) of 4-methyl-2-piperidinecarboxylic acid hydrochloride, 24 g (0.224 mole) of benzyl alcohol and 25.6 g (0.134 mole) of p-toluenesulfonic acid monohydrate in 100 ml of benzene was refluxed for 5 hours with the continuous removal of water through a Dean-Stark water trap. At the end of this period, the solvent was distilled off, and the residue was washed with ether-n-hexane and recrystallized to give 10 g (22%) of benzyl 4-methyl-2-piperidinecarboxylate p-toluenesulfonate, M.P. 160°–163° C.

The following 2-piperdinecarboxylates not previously reported in the chemical literature were synthesized by the aforementioned procedure.

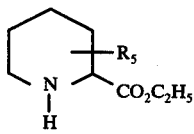

| No. | $R_5$ | Addition moiety | B.P. |
|---|---|---|---|
| 1 | 4-CH$_2$CH$_3$ | — | 82–4° C/3.5 mmHg |
| 2 | 4-CH$_2$CH$_2$CH$_3$ | HCl | |
| 3 | 4-CH(CH$_3$)$_2$ | — | 95–6° C/2 mmHg |
| 4 | 2-CH$_3$ | — | 57° C/3 mmHg |

Having now fully described the invention, it will be apparent to one of ordinary skill in the art that many changes and modifications can be made thereto without departing from the spirit or scope of the invention as set forth herein.

What is claimed as new and intended to be covered by letters patent is:

1. N$^2$-alkoxynaphthylsulfonyl-L-argininamides having the formula:

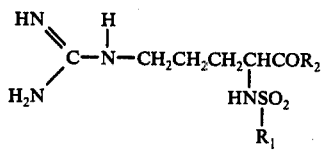

and the pharmaceutically acceptable salts thereof, wherein $R_1$ is naphthyl substituted with at least one $C_1$–$C_5$ alkoxy; $R_2$ is piperidino substituted with —COOR$_3$ wherein $R_3$ is selected from the group consisting of hydrogen, $C_1$–$C_{10}$ alkyl, $C_6$–$C_{10}$ aryl, $C_7$–$C_{12}$ aralkyl and 5-indanyl, said substituted piperidino being optionally substituted with one or more substituents which, alike or different, are selected from the group consisting of $C_1$–$C_{10}$ alkyl, $C_1$–$C_{10}$ alkoxy, phenyl, alkoxycarbonyl or carboxy; and the —COOR$_3$ radical is at the 2 or 3-position of the piperidine radical.

2. The compound of claim 1, having the formula:

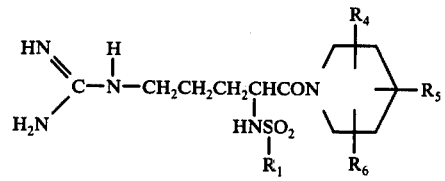

wherein $R_1$ is naphthyl substituted with at least one $C_1$–$C_5$ alkoxy; $R_4$ is —COOR$_3$ located at the 2 or 3-position, wherein $R_3$ is selected from the group consisting of hydrogen, $C_1$–$C_{10}$ alkyl, $C_6$–$C_{10}$ aryl, $C_7$–$C_{12}$ aralkyl and 5-indanyl; $R_5$ and $R_6$ are independently selected from the group consisting of hydrogen, $C_1$–$C_{10}$ alkyl, $C_1$–$C_{10}$ alkoxy, phenyl and carboxy; and $R_5$ and $R_6$ are at the 2, 3, 4, 5 or 6-position of the piperidino radical.

3. The compound of claim 2, wherein $R_1$ is naphthyl substituted with one or two $C_1$–$C_3$ alkoxy; $R_3$ is selected from the group consisting of hydrogen, $C_1$–$C_{10}$ alkyl, $C_6$–$C_{10}$ aryl, $C_7$–$C_{10}$ aralkyl and 5-indanyl; $R_5$ and $R_6$ are independently selected from the group consisting of hydrogen, $C_1$–$C_6$ alkyl, $C_1$–$C_6$ alkoxy, phenyl and carboxy; and $R_5$ and $R_6$ are at the 2, 4 or 6-position of the piperidino radical.

4. A method for inhibiting activity and suppressing activation of thrombin in vivo, which comprises introducing into a mammal a pharmaceutically effective amount of an N$^2$-alkoxynaphthylsulfonyl-L-argininamide having the formula:

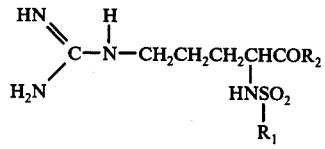

or the pharmaceutically acceptable salt thereof, wherein $R_1$ is naphthyl substituted with at least one $C_1$–$C_5$ alkoxy; $R_2$ is piperidino substituted with —COOR$_3$ wherein $R_3$ is selected from the group consisting of hydrogen, $C_1$–$C_{10}$ alkyl, $C_6$–$C_{10}$ aryl, $C_7$–$C_{12}$ aralkyl and 5-indanyl, said substituted piperidino being optionally substituted with one or more substituents, which, alike or different, are selected from the group consisting of $C_1$–$C_{10}$ alkyl, $C_1$–$C_{10}$ alkoxy, phenyl, alkoxycarbonyl or carboxy; and the —COOR$_3$ radical is at the 2 or 3-position of the piperidino radical.

* * * * *